(12) United States Patent
Benedict

(10) Patent No.: US 6,170,973 B1
(45) Date of Patent: Jan. 9, 2001

(54) METHOD AND APPARATUS FOR WIDE-ANGLE ILLUMINATION IN LINE-SCANNING MACHINE VISION DEVICES

(75) Inventor: George J. Benedict, Alameda, CA (US)

(73) Assignee: Cognex Corporation, Natrick, MA (US)

(*) Notice: Under 35 U.S.C. 154(b), the term of this patent shall be extended for 0 days.

(21) Appl. No.: 08/979,261

(22) Filed: Nov. 26, 1997

(51) Int. Cl.[7] ........................................................ F21V 7/04
(52) U.S. Cl. ............................... 362/554; 361/17; 361/347
(58) Field of Search ................................... 362/551, 554, 362/560, 297, 298, 347, 346, 16, 17; 385/115, 119, 121; 358/509, 510; 348/131

(56) References Cited

U.S. PATENT DOCUMENTS

| | | |
|---|---|---|
| 3,799,679 | 3/1974 | Simko . |
| 4,011,403 | 3/1977 | Epstein et al. . |
| 4,876,455 | 10/1989 | Sanderson et al. . |
| 4,914,553 | 4/1990 | Hamada et al. . |
| 5,038,258 | 8/1991 | Koch et al. . |
| 5,117,312 * | 5/1992 | Dolan .................... 359/858 |
| 5,155,775 | 10/1992 | Brown . |
| 5,172,005 | 12/1992 | Cochran et al. . |
| 5,367,439 | 11/1994 | Mayer et al. . |
| 5,461,417 | 10/1995 | White et al. . |
| 5,475,415 | 12/1995 | Noethen . |
| 5,640,380 | 6/1997 | Saimi et al. . |

FOREIGN PATENT DOCUMENTS

| | | | |
|---|---|---|---|
| 4031633 * | 4/1992 | (DE) | ................................ 362/551 |
| 0021093 * | 5/1980 | (EP) . | |
| 2273976 * | 7/1994 | (GB) | ................................ 362/551 |
| 6-249632 | 9/1994 | (JP) . | |

* cited by examiner

Primary Examiner—Sandra O'Shea
Assistant Examiner—Peggy A Neils
(74) Attorney, Agent, or Firm—William A. Loginov (57) ABSTRACT

A wide-angle illuminator for machine vision applications comprises a fiber optic bundle having a tail end defining a long narrow illumination line adjacent the workpiece and a head end defining a rectangular inlet adjacent the light source. The light source comprises a lamp located within a concave, elliptical cross-section reflector that is elongated in one direction. The elliptical cross-section is the same across the entire direction of elongation, thus defining a partial elliptical cylinder, which is preferably capped by flat, reflective surfaces at each end. The lamp, particularly the filament of the lamp, is aligned with one focus of the ellipse. The head inlet of the fiber optic bundle is aligned with the second focus of the ellipse so that the light emitted from the lamp is reflected to the second focus for transmission through the fiber optic bundle. The resultant light pattern projecting at the tail exhibits an angular light distribution that is weighted toward light that projects at an angle to the optical plane of the tail-end fibers. Light projecting directly perpendicular to the optical plane of each fiber is, likewise, minimized. The resulting distribution increases light at the edges of the field of view, improving camera response across the entire field.

17 Claims, 9 Drawing Sheets

METHOD AND APPARATUS FOR WIDE-ANGLE ILLUMINATION IN LINE-SCANNING MACHINE VISION DEVICES

FIELD OF THE INVENTION

This invention relates to a method and apparatus for providing an illumination line to a workpiece that is viewed by a wide-angle line scan camera, and more particularly to an illumination line that enhances line scan camera performance.

BACKGROUND OF THE INVENTION

Moving webs and other workpieces are often scanned for defects or known patterns using a machine vision device. Machine vision devices typically employ an illumination system to concentrate a bright light into a narrow line along the workpiece. A line scan camera is directed at the illuminated area to receive light from the web. The camera can be oriented to view a direct reflection or transmission of the image as produced by the illumination light. This is termed a so-called "bright field" image. Conversely, the camera can be oriented off-axis relative to the reflected or transmitted is image light, resulting in a so-called "dark field" image.

Figure 1:
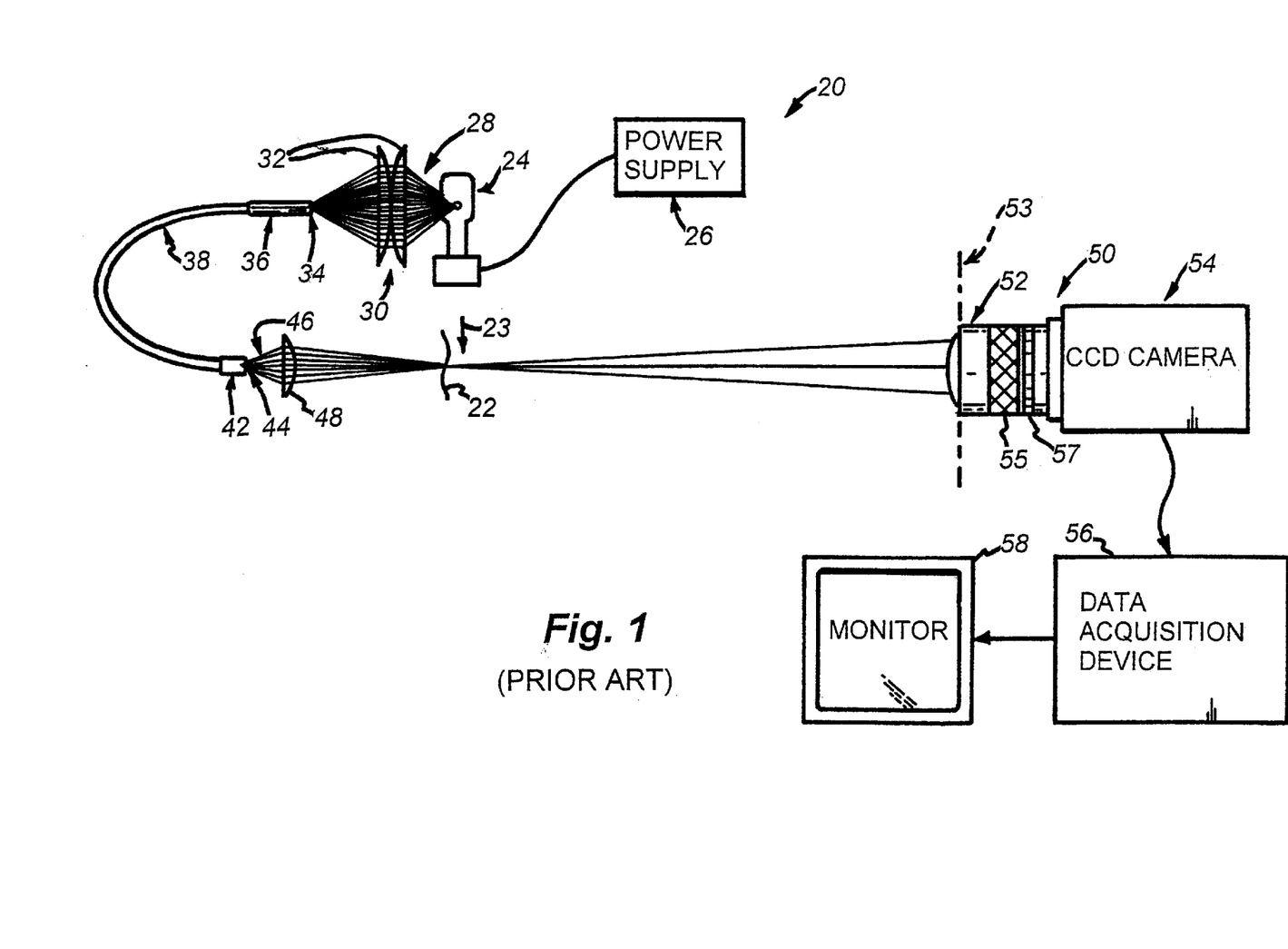
FIG. 1, previously described, is a schematic diagram of a machine vision system with a fiber optic illumination assembly according to the prior art.

FIG. 1 schematically illustrates a machine vision system 20 adapted for use with a wide moving web 22. Width is taken in the direction perpendicular to the page and the web moves in the direction of the arrow 23. The web 22 in this embodiment is a transparent or translucent web in which light is transmitted from one face of the web material to an opposing face. The concepts described are also applicable to an opaque web with certain modifications to be described below. The web 22 is typically wide (about four or more feet wherein width is taken in a direction into the page). A single system 20 can view a web section approximately four feet wide. For web widths greater than four feet, a plurality of identical machine vision systems are arranged side-by-side along the web width. A lamp 24, with an associated power supply 26, generates a bright illumination light that is represented as a series of rays 28. The lamp 24 can be any acceptable bright illumination source such as a metal-halide lamp, a high-pressure sodium lamp, a filament lamp, a laser or other coherent light source, a gas discharge lamp, or an LED array or other semiconductor light source. A 750-watt quartz-tungsten-halogen (QTH) lamp is used in one known illumination arrangement. While not shown, a reflector or shield may be provided so that light emanates only from a predetermined region of the lamp 24. A condenser lens assembly 30 is provided adjacent the lamp 24. In this embodiment, a condenser assembly 30 comprises two or more counterfacing plano-convex lenses 32. The lenses have a circular perimeter, forming a focused beam that projects a circular pattern. At the desired focal point 34 of the rays 28 is positioned the head or "entrance face" of a fiber optic cable 38.

Figure 2:
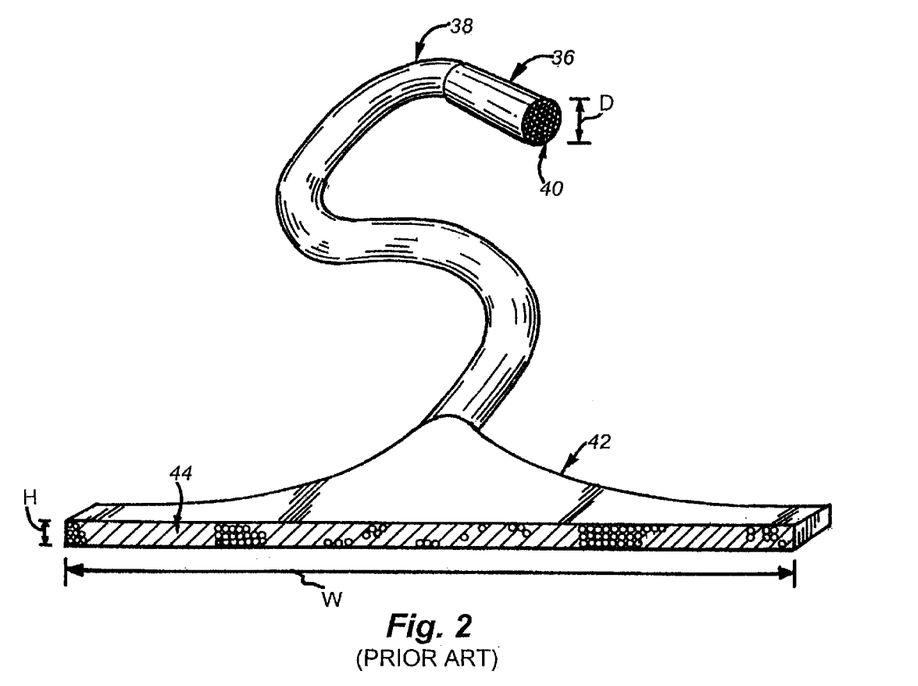
FIG. 2, previously described, is a somewhat-schematic perspective view of the fiber optic illumination assembly for use in the prior art system of FIG. 1.

With further reference to FIG. 2, the fiber optic cable assembly is shown in further detail. The head 36 of the cable 38 reveals a fiber optic bundle 40 constructed from a large number of small-diameter fiber optic strands with flat, polished ends. The cable 38 typically comprises a resilient outer covering that encases over three-hundred-thousand 0.002-inch diameter optical fibers. Typically, the fibers are packed to substantially fill the cross-sectional area of the cable 38. The diameter D of the head 36 is approximately 1.35 inches, and is approximately equal to the diameter of the spot generated by the rays 28. In other words, the head 36 is located relative to the condenser lens assembly 30 so that the illumination spot approximately covers the head 36. Note that the amplitude of the distribution within this spot may not be uniform.

At the opposing tail or "exit face" of the cable 38 is located an illumination line housing 42. The line housing 42 includes an elongated rectangular opening 44 that reveals the polished tail ends of the cable's individual optical fibers. The line housing opening 44 and a typical implementation has a width W of four feet and a height H of 0.030 inch. In general, ten to twenty fibers can be aligned vertically side-by-side within the confines of the height H.

The long, narrow line of bundled optical fibers within the line housing 42 generates a corresponding narrow elongated line of light rays 46 that are typically refocused by an elongated focusing lens 48. Randomization of the fibers between the head and tail ends of the cable generally tends to improve the uniformity of the resulting illumination line. In fact, it is common to twist and braid the fibers within a cable to achieve greater uniformity in transmitted light distribution. However, the system may rely on a certain rotational orientation of the head end relative to the illumination source (e.g. the light bulb), and rotation of the head end relative to the source at a later time may disturb the system's settings. In addition, the particular distribution of light produced may limit the ability to subsequently move the camera relative to the image line. Thus the randomization can be both advantageous and problematic.

A variety of lens constructions can be used such as a linear convex cylinder lens or an acrylic rod lens approximately one inch in diameter. An off-axis elliptical reflector can also be employed. The term "lens" should be taken broadly to include a focusing reflector. The lens 48, focuses the rays 46 onto the web 22 to generate the desired narrow illumination line across the width of the web 22. Based upon this illumination line, light is transmitted through the web 22 to a camera assembly 50 that comprises a wide-angle focused lens 52 and an electro-optical pick up assembly, such as a commercially available CCD camera unit 54. The lens 52 is focused on the web 22 using the focus ring 55 and a desired lens aperture is provided using the aperture adjustment ring 57. Images are converted by the CCD camera into electronic signals for transmission to an appropriate data acquisition device 56. The device can comprise a microcomputer having pattern-recognition software for analyzing the surface of the viewed on the web. A monitor 58 can also be provided for real-time of viewing of the web surface or for viewing data derived by the software.

Figure 3:
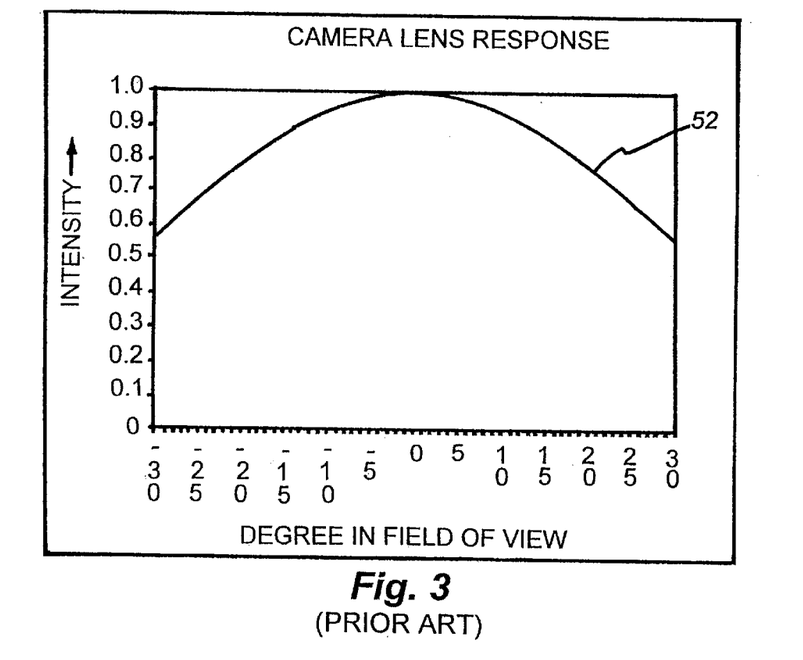
FIG. 3, previously described, is a graph detailing a measured camera lens response versus angle of view for the prior art system of FIG. 1.

One problem encountered with the machine vision system described above is that the quality of the substantially uniformly illuminated image viewed by the wide-angle lens tends to degrade near the edges of the field of view of the lens. This degradation is due largely to the inherent optical characteristics of wide-angle lenses. FIG. 3 illustrates the camera lens response measured by the CCD element 54 for a 35 mm Nikon Nikkor™ lens. The specified field of view of this lens is ±32° from perpendicular (0°, directly beneath the camera) which translates into approximately four feet of web width at a focal length of approximately 3.2 feet from the web face to the camera'optical plane 53. The measured response curve 52 registers 100 percent intensity at a 0° field of view. In other words, maximum intensity is viewed directly beneath the lens. As the viewing angle increases, the viewed intensity drops off sharply. The decrease in intensity occurs as a function of the cosine to the fourth power of the camera's field of view angle. At maximum viewing angles the intensity of the viewed image is about 52 percent of the maximum value. This uneven response can lead to viewing errors since illumination at the edges of the field of view may be insufficient to acquire a proper image of the web. Another associated problem with the prior art illumination arrangement is that the camera operates most effectively when it is aligned near the center of the illumination line. Placing the camera "off-axis" can result in a significantly degraded acquired image.

There are several techniques currently employed to overcome the imaging limitations of wide-angle lenses. One technique entails providing additional illumination near the edges of each camera's field of view. Cameras can be placed closer together so that the full field of view of each camera is not utilized. This and other solutions to the problem, however, substantially increases equipment cost and reduces efficiency. Conversely, some of the light near the center of the field of view can be attenuated using various types of well-known apodizers so that the overall image appears more-even across the viewing range. These attenuation techniques, however, often reduce the image quality since the total amount of light entering the lens is reduced.

It is, therefore, an object of this invention to provide a method and apparatus for providing an illumination line that enhances the response of a wide-angle lens at the edges of its field of view. This illumination line should not require any attenuation of light entering the camera lens and should not require any decrease in the rated field of view of the lens. Furthermore, the choice of the position of the camera along the illumination line should not influence the benefits of the illumination line provided according to this invention.

SUMMARY OF THE INVENTION

An illumination device and a method for illuminating a workpiece overcomes the disadvantages of the prior art by projecting, across a predetermined width of the workpiece, an illumination line that naturally compensates for the degradation of the response of a machine vision camera's wide-angle lens near the edges of its field of view. This compensation results from the generation of an illumination line with light having an angular distribution that favors non-perpendicular rays, and more particularly rays oriented at approximately ±30° to perpendicular. This characteristic angular distribution increases the number of rays entering the wide-angle camera lens at the edges of the field of view relative to the center of the field of view, thus enhancing the uniformity of the image.

According to a preferred embodiment, light from a source, having a special angular distribution of rays, illuminates the rectangular-shaped head (or "inlet") of a fiber optic cable. The characteristic angular distribution is present in each fiber optic strand, and is preserved in the collective output from the tail (or "outlet") of the fiber optic cable. The elongated, narrow light output from the tail of the fiber optic cable is focused on the workpiece, resulting in a corresponding elongated, narrow light line, which is then observed by the wide-angle camera lens.

A precision quartz-tungsten-halogen (QTH) lamp is employed in a concave reflector cavity shaped as an elongated partial elliptical cylinder. The cross-section of the partial elliptical cylinder is defined by a major axis, a minor axis and two foci. The lamp filament is preferably centered with respect to the direction of elongation of the cylinder. The filament is positioned on the major axis at the nearest focal point to the cylinder's reflector surface. Similarly, the fiber inlet is preferably centered on the major axis at the more-remote focal point. This positional relationship causes light generated at the filament to be reflected off the reflector surface back to the remote focal point, where it is concentrated into a substantially uniform rectangular shape. This reflector geometry naturally generates the advantageous angular distribution of rays described above.

A plurality of light sources and fiber optic cable assemblies can be employed in a side-by-side relationship to serve a single camera. A variety of focusing lenses can be employed to focus the illumination line to a desired width onto the workpiece. The camera can be mounted at a desired focal length adjacent an opposing face of the workpiece relative to the cable outlet where the workpiece is transparent or translucent. Conversely, the camera can be mounted adjacent the same face as the outlet where the workpiece is opaque, receiving light reflected from the face. Finally, it is contemplated that the camera can be positioned at a variety of points along the illumination line relative to a center position on the illumination line.

BRIEF DESCRIPTION OF THE DRAWINGS

The foregoing and other objects of and advantages of the invention will become more clear with reference to the following detailed description as illustrated by the drawings in which.

DETAILED DESCRIPTION

Figure 4:
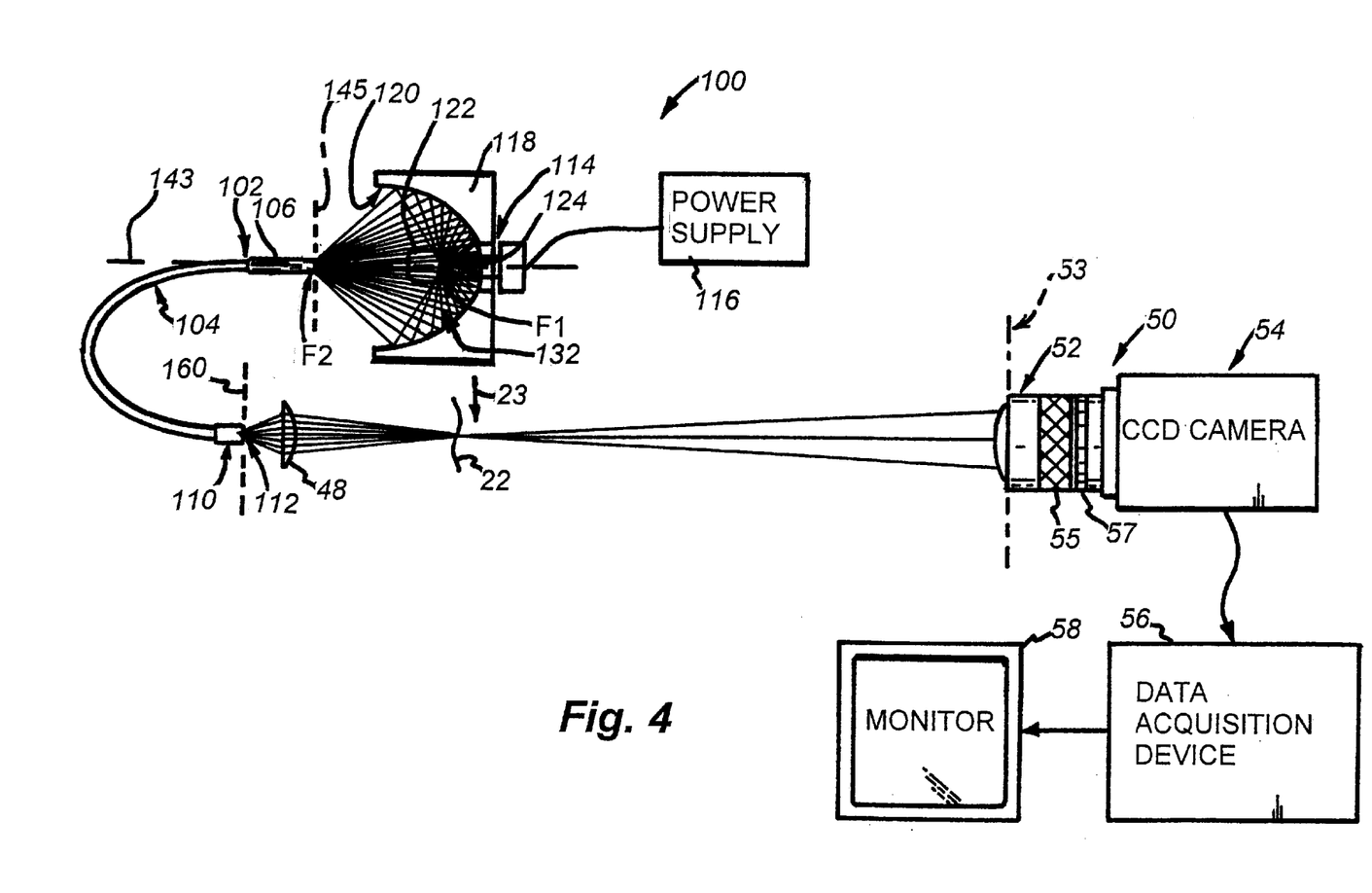
FIG. 4 is a schematic diagram of a machine vision system including an illumination assembly according to a preferred embodiment of this invention.

A wide-angle machine vision system 100 with an illumination assembly according to an embodiment of this invention is detailed in FIG. 4. The camera 50, data acquisition device 56, monitor 58, web 22 and focusing lens 48 are similar to those described above with reference to the prior art system of FIG. 1. Accordingly, like reference numerals are used to describe these elements. Briefly, the camera 50 acquires light from an illumination line projected by the illumination assembly 102 onto a translucent or transparent web or other workpiece 22. The web 22 is generally moving, and can be opaque according to an alternate embodiment described below. The received light is processed by a data acquisition device 56, which can comprise a computer, and processed data and images are viewed by an operator through a monitor 58. Note that the camera's image plane 53 is approximately parallel to the surface of the web 22 in this embodiment. The camera can be oriented at a variety of angles relative to the web 22 according to this invention.

Figure 5:
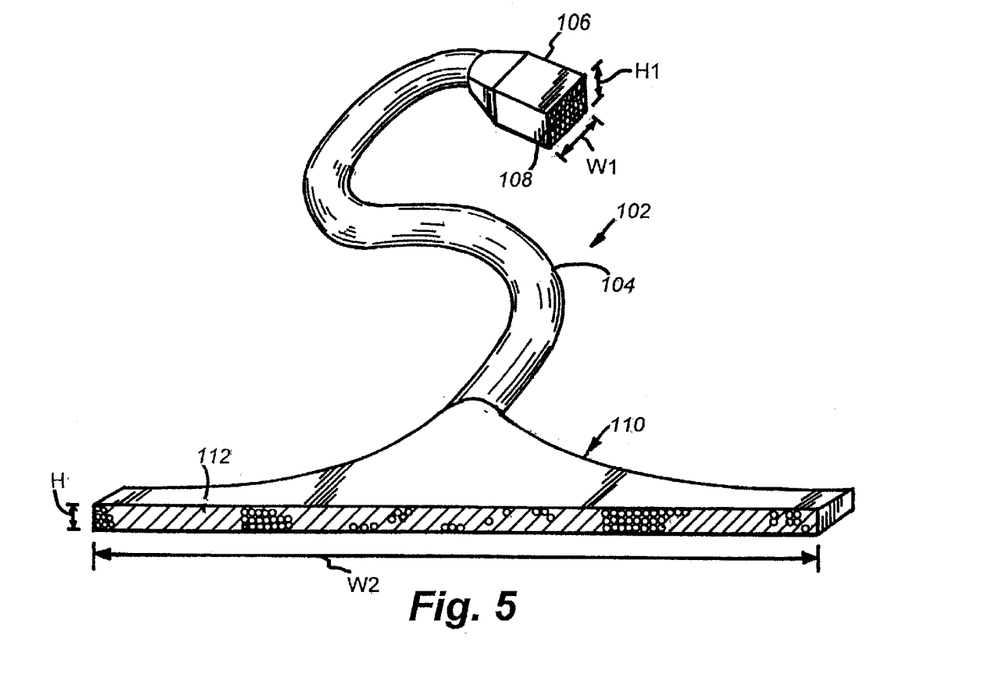
FIG. 5 is a somewhat-schematic perspective view of a fiber optic illumination assembly according to this invention.

With further reference to FIG. 5, the illumination assembly 102 of this embodiment includes a fiber optic cable 104 that comprises an outer resilient covering surrounding a densely packed bundle of individual optical fibers. The fiber optic cable head 106, unlike the prior art, is arranged with a rectangular head inlet 108. The depicted rectangle has a width W1 of approximately 2 inches. It has a height H1 of approximately 0.1 8 inch.

Figure 5A:
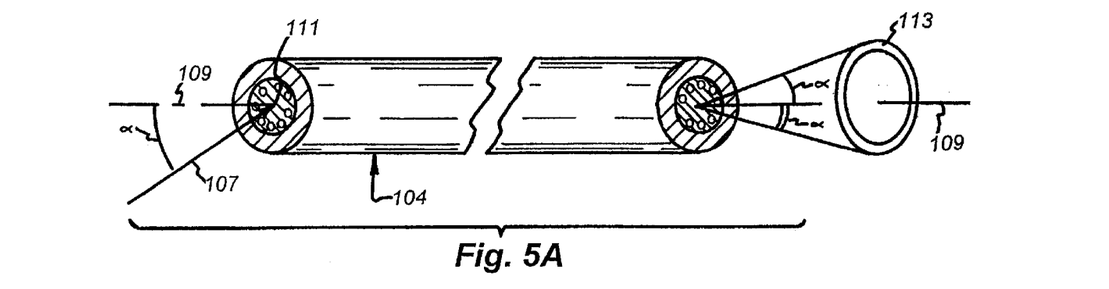
FIG. 5A is a somewhat-schematic perspective view showing the characteristic distribution of projected light produced when an incident ray passes through a fiber optic cable.

Briefly, by way of background, FIG. 5A details the resulting diffuse conical distribution achieved when light rays 107 strike a single fiber of the cable 104 at an oblique incident angle $\alpha$ relative to a perpendicular axis line 109 taken through the face 111 of the fiber. The rays gradually disperse in azimuth along the length of the fiber so as to fill in an annulus 113 of a cone of half-angle $\alpha$ as the rays exit the fiber. This characteristic transmission through the fiber is employed to provide an effective wide-angle illumination assembly according to this invention.

Each fiber in the cable bundle is approximately 0.002 inch in diameter. Typically, fibers having a numerical aperture of approximately 0.60 are employed with a maximum half-angle $\alpha$ of approximately 37°.

Figure 6:
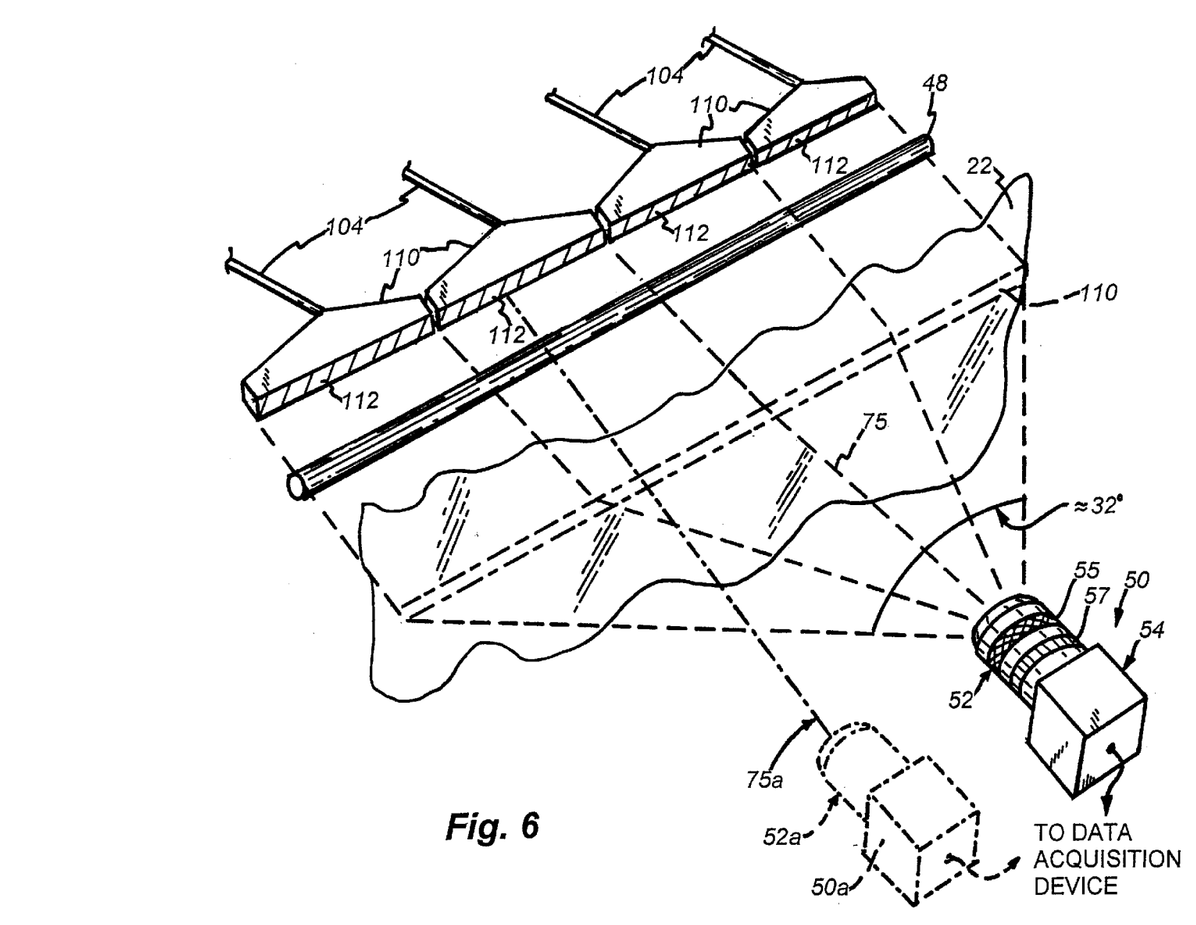
FIG. 6 is a somewhat-schematic perspective view of a series of line illuminator housings mounted in a side-by-side arrangement according to an embodiment of this invention.

With reference again to FIG. 5, the line housing 110 at the cable's tail end includes an outlet 112 consisting of a bundle of polished fiber optic strand ends. The outlet has a height H of 0.030 inch and a length W2 of 12 inches. The length W2 is one-fourth that of the length W for the prior art illumination line housing depicted in FIG. 2. The exact length of the line housing outlet 112 can be varied. An outlet length of twelve inches is chosen as a convention in this embodiment. This line housing, consequently, projects a twelve-inch illumination line onto the web or other workpiece being scanned. In general, a plurality of line housings are joined together in an appropriate frame to provide the desired length of illumination line. Typically, each wide-angle lens can view a line of approximately 4 feet. As detailed in FIG. 6, four line housings 110 are joined side-by-side to produce the desired illumination line 111 on the web 22. Each line housing is connected by an identical fiber optic cable 104 to an individual light source as described hereinbelow. A variety of mounting brackets (not shown) can be used to hold the housings 110 and the lens 48 in position over the web 22. Therefore, while this description shall make reference to a single line housing and light source, it should be understood that a plurality of light sources, fiber optic cable assemblies and line housings may be combined to serve a single camera. Conversely, a plurality of successive cameras could be illuminated by a single light line source.

It is expressly contemplated that the camera can be mounted "off-axis" relative to the center region of the image line generated by its associated illumination assembly(ies). Each image line has approximate "edges," at which intensity falls off substantially. Between these edges, typically at a midpoint of the housing(s), is located a center region. The camera 50 has an optical axis 75 approximately aligned with the center region. Conversely FIG. 6 also depicts a camera 50a (shown in phantom) located in an off-axis position relative to the center region as delineated by the housing outlets 112. The optical axis 75a of the lens 52a is shown particularly to the left of the centered camera 50. The unique angular distribution of light provided by the illumination assembly according to this invention (described further below) enables placement of the camera at a wide range of non-centered positions. Such placement is expressly contemplated according to this invention.

While twelve-inch outlets are detailed according to this embodiment, it is expressly contemplated that a longer single line can be provided according to this invention. The overall surface area of the rectangular line housing is increased in proportion with the increase in width of the line housing. This requires a comparable increase in the size of the inlet area, since the number of fiber optic strands also increases. Typically, the height H of the line housing opening does not vary as a function of illumination line length. Furthermore, different fiber optic diameters could be used, for example 0.001 inch or smaller.

Figure 7:
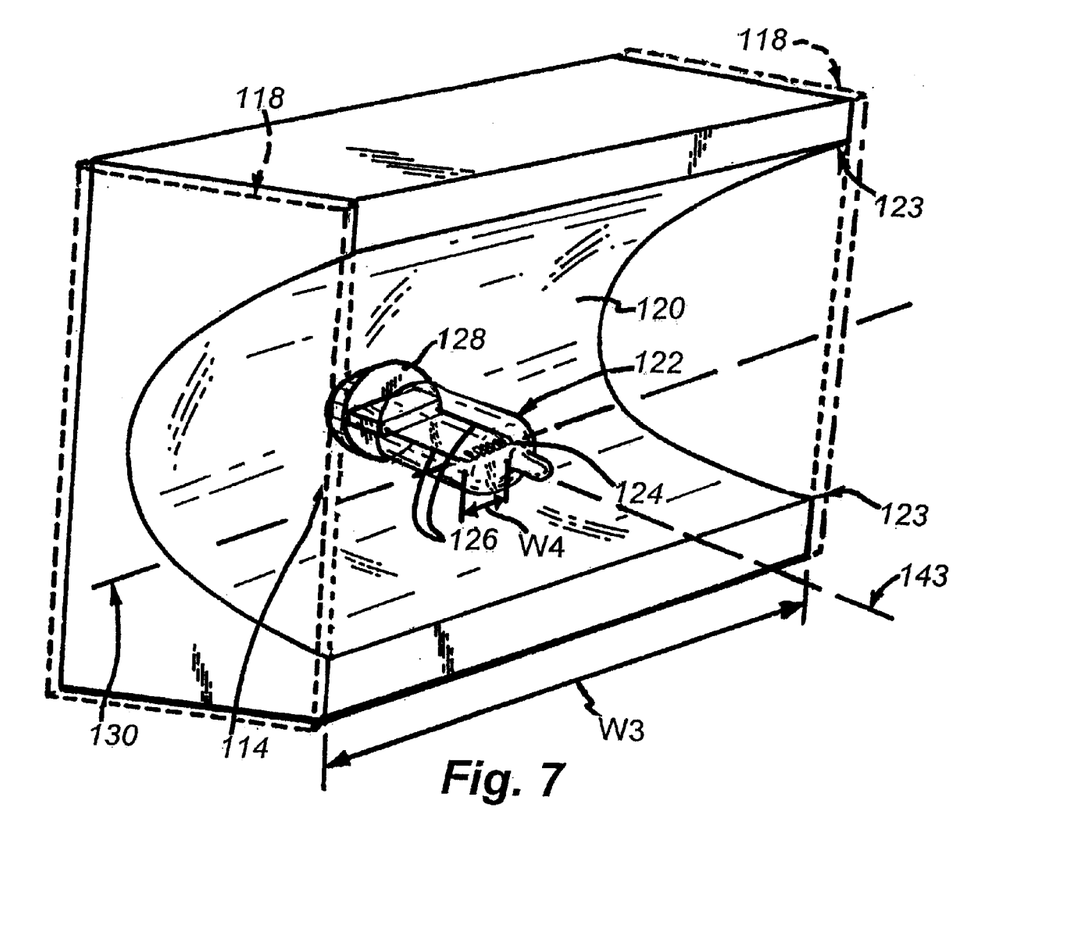
FIG. 7 is perspective view of an illumination reflector and lamp according to this invention.

Illumination light is provided to the fiber optic assembly 102 by a lamp assembly 114 interconnected with a power supply 116. With reference also to FIG. 7, the lamp assembly is mounted in a reflector assembly 118 defining a concave reflector surface 120. The reflector surface 120 has a surface shape that, in cross-section, defines a partial ellipse. The dimensions of the ellipse are substantially constant across the entire width W3 in this embodiment. The reflector is said to be "elongated" in the direction of the width. In other words, if the reflector surface were cut in a direction transverse to the direction of elongation (e.g. along a plane perpendicular to W3) at any point along that direction, then the shape defined by the elliptical cross-section would remain substantially constant. As used herein, such a reflector shall be termed "a partial elliptical cylinder."

The reflector assembly 118 is capped at each side by a respective cover 131 or "end cap" (shown in phantom in FIG. 7). The covers 131 each have a reflective inner surface facing each other. The function of the covers 131 is described further below. the covers can be omitted according to an alternate embodiment, or can comprise non-reflective covers.

Figure 8:
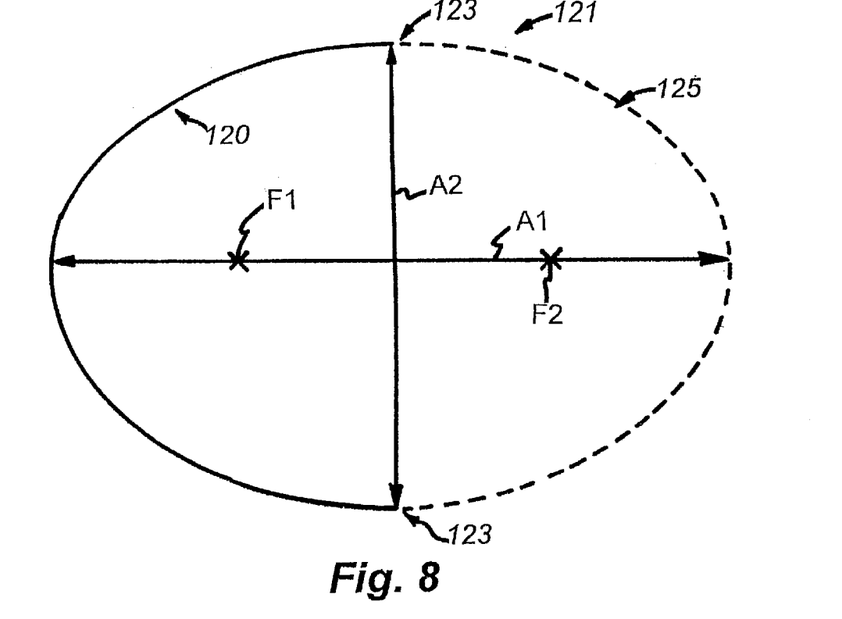
FIG. 8 is a schematic side view of the cross-sectional geometry of the illumination reflector of FIG. 7.

FIG. 8 details the cross-sectional geometry of the elliptical reflector surface 120 according to this embodiment. The reflector surface 120 (solid line) is part of a complete ellipse 121. The ellipse is defined by a major axis A1 and a shorter, minor axis A2. The surface 120 is symmetrical about the major axis A1, and has upper and lower edges 123 that lie upon the minor axis A2. The discontinued portion of the ellipse defines a phantom line 125 extending symmetrically around the major axis A1. The resulting ellipse defines two focus points F1 and F2 (see also FIGS. 4 and 8) at points, respectively, adjacent to and remote from the reflector surface 120. In this embodiment, the major axis A1 is approximately 3.15 inches, the minor axis is approximately 2.45 inches and the foci F1 and F2 are each spaced approximately 1 inch from the respective adjacent intersection of the major axis A1 with the minor axis A2.

The lamp 122 of this embodiment comprises a precision 75-watt quartz-tungsten-halogen (QTH) bulb available from a variety of sources, such as Gilway Technical Lamp Company. A "precision" lamp displays an accurate, consistent distance between the filament and mounting base. The central filament 124 is mounted on a pair of support wires 126 that extend down to a precision two-pin socket 128. Other socket arrangements can be utilized where appropriate. The filament has width W4 of approximately 0.2 inch and the filament's coil diameter is approximately 0.04 inch. The filament projects outwardly on its base wires 126 approximately 0.625 inch from the reflector surface 120. The width W3 of the reflector surface 120 is 2 inches in this embodiment. The reflector is constructed from a solid billet of metal, such as aluminum in this embodiment. It is generally formed using machining processes. It can also be formed using casting, extrusion or other acceptable processes. The exposed reflector surface 120 is typically polished and silvered using known techniques to provide a highly reflective surface finish. An addtional layer of either inconel or copper is typically applied to the reflector surface 120 to protect it from the environment.

As shown in FIG. 4, the lamp filament 124 extends approximately parallel to the direction of elongation along a line 130 (see FIG. 7) defined by the adjacent focus points F1. Likewise, the head 106 of the cable 104 is positioned so that its face 108 is centered at the opposing, remote focus point F2, and aligned about a central line 143 that is collinear with the ellipses' major axis A1. In particular, the optical plane 145 of the face 108 perpendicularly transects the major axis A1 at the remote focus F2. The width W1 of the rectangular cable head 106 and the width W3 of the reflector are approximately equal at 2 inches. It is contemplated that the side edges or the reflector and the inlet substantially overlap whereby the reflector transmits its full width of light into the inlet.

The geometry of the partial elliptical reflector causes the light rays 132 emanating from the filament 124 at focus F1 to converge at the focus F2. Hence, these rays 132 converge at the face 108 of the cable head 106. Each strand of the fiber optic bundle transmits the received focused light to the outlet at the cable tail 110, where it is projected in a resulting thin line onto the web 22. In general the projected beam is composed of hundreds of thousands of smaller beams, which each respective fiber optic strand carries without substantially altering the characteristics of the light received at the cable head 106.

Figure 8A:
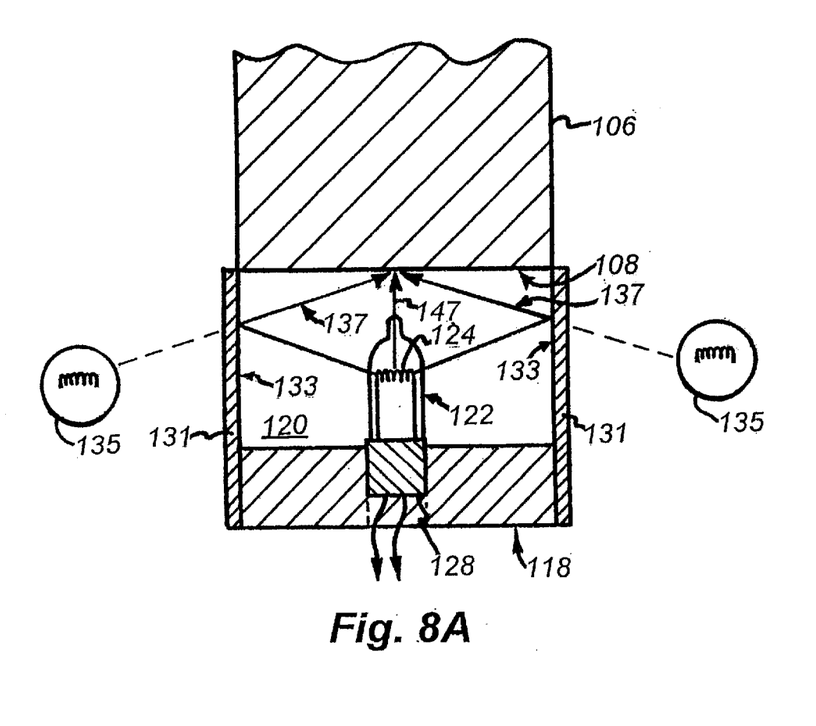
FIG. 8A is a top cross-section of the illumination reflector and lamp of FIG. 7 interconnected with the head end of the fiber optic cable.

With reference to the top cross-section of the reflector assembly 118 detailed in FIG. 8A, the function of the covers 131 is now described. The substantially flat, reflective inner surface 133 of each cover defines a corresponding "virtual" image 135 (rays 137) of the filament 124 that is projected onto the face 108 of the cable head end 106 along with the "real" image (ray 147). The combined real and virtual images enhance the distribution of light according to this embodiment. Although the light entering the head of the cable is generally more uniform than that of the prior art arrangement, the randomization of fibers (described in the Background, above) tends to further improve the uniformity of light exiting the tail end. Note also that the covers are aligned with the side edges of the head end 106, ensuring that a minimum amount of light is lost between the lamp and the cable.

Using the camera 50 which comprises a CCD element 54 and a 35 mm Nikon Nikkor™ wide-angle lens, the characteristics of the light transmitted from the outlet 110 are measured. The camera lens is focused onto the web surface 22 from a distance of approximately 3.2 feet, by adjusting the focus ring 55 until desired clarity is obtained. The CCD element 54 utilized in the camera 50 is a Reticon™ series line scan CCD element available from EG&G. It operates at 40 Mhz signal transmission speed and derives a 10-bit per pixel grayscale output with a total of 2,048 pixel elements. An appropriate housing is used for the element, and a standard quick-detach bayonet mount is used to interconnect the lens 52 to the housing.

Figure 9:
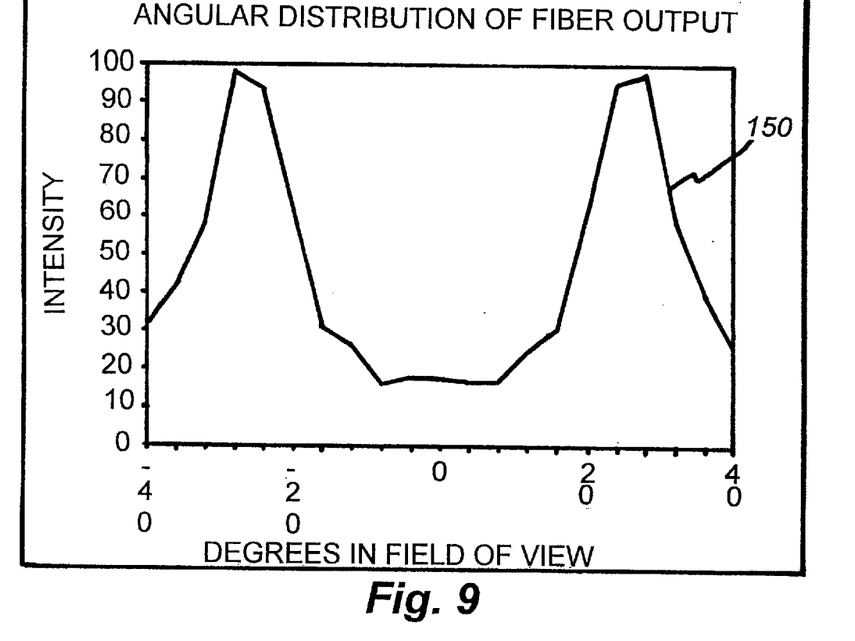
FIG. 9 is a graph detailing the angular distribution of light versus angle of view for the system of FIG. 4.

FIG. 9 illustrates a curve 150 indicating the specific angular distribution of light obtained using the elliptical reflector surface 120 of this invention. The majority of light, from an angular standpoint, exits the optical plane 160 (see FIG. 4) of a tail end of each of the fibers at approximately ±30° from perpendicular to the plane 160 (where perpendicular is considered "straight out" of the fiber).

Figure 10:
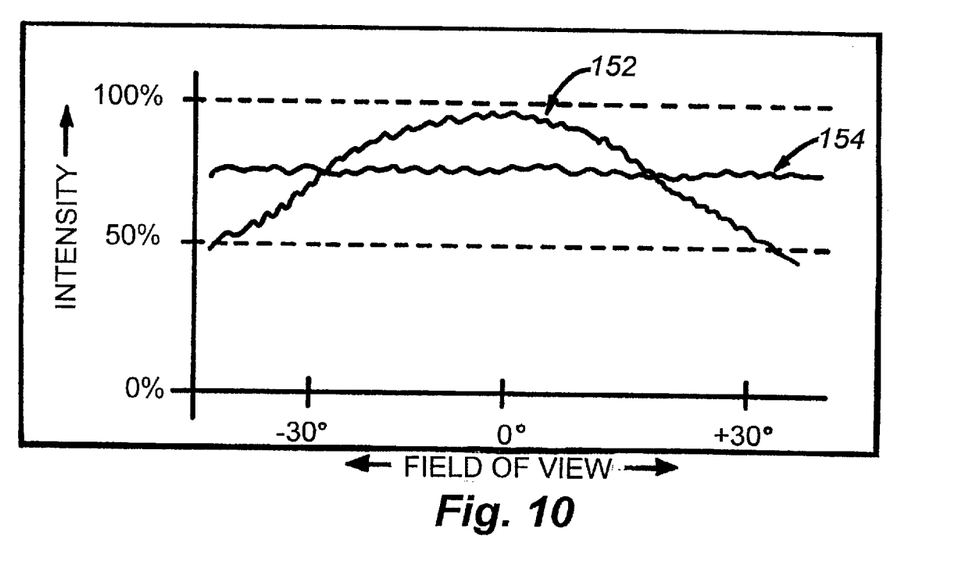
FIG. 10 is a graph detailing the camera lens response versus the angle of view for the system of FIG. 4.

Thus, the elliptical reflector surface 120 of this invention naturally minimizes light that is incident directly into the center of the lens (without loss of overall light), and favors light oriented at an angle to the optical plane 53 of the lens. Using the prior art illumination arrangement, the camera records the response curve 152 as depicted in FIG. 10. The highest measured intensity is, as expected, attained at 0° field of view, and the measured intensity decreases by about 48 percent at the far edges of the field of view (approximately ±32°). In comparison, using the illumination arrangement according to the preferred embodiment of this invention, the angular distribution of light described in FIG. 9 produces the measured response curve 154. This curve displays a flat, relative 60–70 percent intensity across the entire field of view. Hence response at the edges of the field of view is sufficient to provide a uniform, wide-angle image to the CCD element. The overall intensity of light can, likewise, be increased and decreased by adjusting the source lamp intensity to provide an optimal light level to the CCD element. Note that the flat curve attained as a result of a desirable angular distribution of rays according to this invention facilitates placement of the camera off-axis along the image line as described above (see FIG. 6). The illumination line will result in a substantially flat response curve, regardless of the placement of the camera along the line. This is a particularly desirable outcome, since it enables cameras to be positioned more freely, reducing potential mounting problems on large, complex machines, and enabling specific cameras to focus on particular points of interest within a larger inspection area without regard to the center of the illumination line.

By favoring light oriented at angles to the perpendicular axis (e.g. 0°) of the field of view, the illumination of the edges of the camera's field of view is enhanced. This enhancement occurs advantageously without attenuation at the lens.

Figure 11:
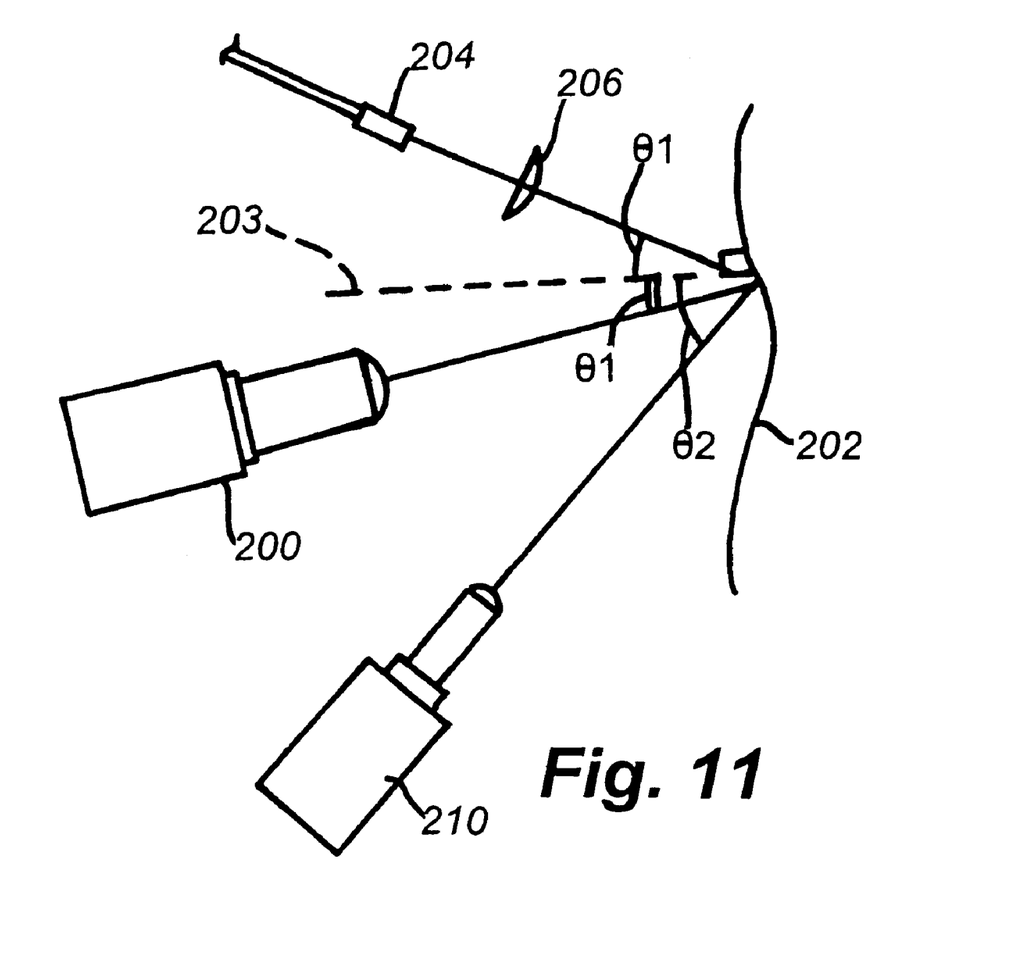
FIG. 11 is a schematic side view of an illumination assembly and camera, according to an alternate embodiment of this invention, oriented to scan an illuminated line on an opaque surface.

While the illustrated embodiment details a transparent or translucent web 202 in which light is transmitted from the illuminator, through the web, to the camera, FIG. 11 illustrates an embodiment in which the camera 200 is positioned on the same side of the web 202 as the illumination assembly line housing 204 and focusing lens 206. The light path from the line housing 204 to the camera 200 occurs by reflection off of the web 202. Typically, the line housing 204 and camera 200 are located at equal angles θ1, relative to a perpendicular line 203 through the web when a bright field image is to be viewed. This angular offset prevents the illuminator from blocking the camera's view. The tail 204 of the cable differs from that of FIG. 4 in its specific mounting orientation relative to the web 202 and the camera 200. The light source and camera arrangement are otherwise identical.

A dark field image can, likewise be obtained by positioning a camera 210 at an angle θ2 that is unequal to the angle θ1. Hence, the camera 210 views an image that is not composed of light directly reflected off the web from the illuminator. Note that the dark field camera arrangement can be utilized with a transmissive web by orienting the camera at an angle not directly aligned with the axis of the illuminator. Such an arrangement is expressly contemplated according to this invention.

It should be noted that a variety of mounting brackets and arrangements are contemplated for maintaining the above-described components in a secure relationship relative to each other. The mounting arrangement utilized depends upon the particular orientation of the workpiece and any associated processing components. Various adjustment mechanisms for relocating components relative to each other can also be employed. Such brackets and the like should be readily implemented by those of ordinary skill.

In addition, while a partial ellipse is described as the preferred cross-section for a concave reflector according to this invention, it is contemplated that an imperfect elliptical shape constructed, for example from straight or curved segments can be employed. Likewise, the shape may define another form of concave surface that generates the advantageous angular distribution of light described herein.

The foregoing has been a detailed description of a preferred embodiment. Various modifications and additions can be made without departing from the spirit and scope of the invention. For example, a variety of focus lenses can be used at the outlet of the cable. Mirrors can be used, or specially ground elongated lenses can be employed. The size and field of view of the camera lens and the imaging element can be varied. The characteristics of the illumination lamp, can, likewise, be varied. Coherent laser light or light filtered to exhibit a particular color range light can be employed. In some embodiments, light in near-visible or invisible spectra can also be used. The nature of the reflector surface can be varied to best suit these types of light. Similarly, the length of the cable's outlet as well as its height can be varied. Finally, while an overlapping rectangular inlet is used at the head end of the cable, it is contemplated that a variety of inlet perimeter shapes can be employed, it being desirable mainly that a sufficient quantity of reflected light be directed into the inlet form the reflector. Accordingly, this description is meant to be taken only by way of example and not to otherwise limit the scope of the invention.

What is claimed is:

1. A line illuminator for projecting a line of illumination light on a workpiece for receipt by a wide-angle camera comprising:

an optical fiber bundle having a head end and a tail end, the tail end defining an elongated, narrow outlet of optical fibers located adjacent the workpiece and the head end defining a rectangular inlet of optical fibers;

a concave reflector defining a partial elliptical cylinder shape extending in a direction of elongation, with a constant partial elliptical cross-section taken along the direction of elongation, the partial elliptical cross-section defining having a major axis and defining on the major axis a first focus adjacent the reflector surface and a second focus more remote from the reflector surface;

an illumination source located within the concave reflector adjacent the first focus and wherein the rectangular inlet is located adjacent the second focus, whereby light is transmitted from the illumination source and converges at the rectangular inlet for transmission to the outlet with a predetermined angular light output distribution by the optical fiber bundle; and wherein the outer perimeter of the inlet defines a rectangular outer perimeter having a width, taken along a line parallel to the direction of elongation that is approximately equal to a width of the concave reflector taken along the direction of elongation, and wherein the rectangular outer perimeter substantially overlaps the concave reflector.

2. The line illuminator as set forth in claim 1 wherein the illumination source comprises a lamp having a filament, the filament being positioned approximately at the first focus.

3. The line illuminator as set forth in claim 2 wherein the lamp is centered at an approximate midpoint along the direction of elongation.

4. The line illuminator as set forth in claim 1 wherein the partial elliptical cross-section includes a minor axis transverse to the major axis wherein the partial elliptical cross-section is symmetrical about the major axis and includes edges approximately aligned with the minor axis.

5. The line illuminator as set forth in claim 1 wherein the inlet includes an outer perimeter that is centered with respect to the major axis and defines an optical plane transverse to the major axis.

6. The line illuminator as set forth in claim 1 further comprising at least one end cap having a reflective surface located at an end of the concave reflector for projecting a virtual image of the illumination source at the inlet.

7. The line illuminator as set forth in claim 1 further comprising an end cap having a reflective surface located at each of opposing ends of the concave reflector for projecting a pair of respective virtual images of the illumination source at the inlet.

8. A method for projecting a line of illumination light on a workpiece for receipt by a wide-angle camera comprising the steps of:

providing an optical fiber bundle having a head end and a tail end, the tail end defining an elongated, narrow outlet of optical fibers and the head end defining an inlet of optical fibers, including locating the outlet adjacent the workpiece so that light is projected from the outlet onto the workpiece as an elongated illumination line;

providing a concave reflector defining a partial elliptical cylinder shape extending in a direction of elongation for a first distance, with a constant partial elliptical cross-section taken along the direction of elongation, the partial elliptical cross-section defining having a major axis and defining on the major axis a first focus adjacent the reflector surface and a second focus more remote from the reflector surface;

locating a lamp having a filament within the concave reflector including supporting the filament on two base wires that extend from a base located on the reflector so that the filament extends over a second distance, less than the first distance, at an approximate midpoint of the first distance along the direction of elongation and approximately parallel to the direction of elongation at the first focus, and locating the inlet adjacent the second focus, whereby light is transmitted from the illumination source and converges at the inlet for transmission to the outlet with a predetermined light output distribution by the optical fiber bundle;

projecting light from the outlet as a line onto a workpiece with the predetermined light output distribution; and receiving light from the workpiece with the predetermined light output distribution by the wide-angle camera along a camera field of view that extends from an axis line perpendicular to an optical plane of the wide-angle camera out to an edge of the field of view, wherein the predetermined light output distribution is arranged to reduce angular light output aligned with the central line and increase angular light output aligned along a non-perpendicular angle away from the central line, thereby smoothing an intensity of viewed light across the field of view.

9. The method as set forth in claim 8 wherein the step of providing the concave reflector includes defining the partial elliptical cross-section to include a minor axis transverse to the major axis wherein the partial elliptical cross-section is symmetrical about the major axis and includes edges approximately aligned with the minor axis.

10. The method as set forth in claim 8 further comprising centering an outer perimeter of the inlet with respect to the major axis wherein an optical plane defined by the inlet is transverse to the major axis.

11. A method for projecting a line of illumination light on a workpiece for receipt by a wide-angle camera comprising the steps of:
providing an optical fiber bundle having a head end and a tail end, the tail end defining an elongated, narrow outlet of optical fibers and the head end defining an inlet of optical fibers, including locating the outlet adjacent the workpiece so that light is projected from the outlet onto the workpiece as an elongated illumination line;
providing a concave reflector defining a partial elliptical cylinder shape extending in a direction of elongation, with a constant partial elliptical cross-section taken along the direction of elongation, the partial elliptical cross-section defining having a major axis and defining on the major axis a first focus adjacent the reflector surface and a second focus more remote from the reflector surface;
locating an illumination source within the concave reflector adjacent the first focus including locating the inlet adjacent the second focus, whereby light is transmitted from the illumination source and converges at the inlet for transmission to the outlet with a predetermined light output distribution by the optical fiber bundle;
centering an outer perimeter of the inlet with respect to the major axis wherein an optical plane defined by the inlet is transverse to the major axis; and
wherein the step of providing the optical fiber bundle includes defining the outer perimeter to be rectangular in shape having a width, taken along a line parallel to the direction of elongation that is approximately equal to a width of the concave reflector taken along the direction of elongation, and wherein the rectangular outer perimeter overlaps the concave reflector.

12. The method as set forth in claim 8 further comprising variably positioning the camera at a plurality of locations with respect to the workpiece so that the camera is aligned with a plurality of locations along the elongated illumination line.

13. In a machine vision system having a camera with a wide-angle lens for viewing a predetermined width of a workpiece based upon a predetermined field of view, an illumination assembly that improves resolution of a viewed image by the camera at remote, opposing edges of the field of view, the opposing edges being oriented at a predetermined wide-angle to a line perpendicular to an optical plane of the lens, the illumination assembly comprising:
an illumination source that includes a concave reflector having a light element located within an enclosed portion of the reflector, wherein the light element includes a filament that extends over a first width a between two base wires;
a fiber optic cable having a head end defining an inlet, the head end located to receive reflected light from the reflector, the head end defining first ends of a densely packed bundle of optical fibers formed into a first shape having a first width and a tail end, defining opposing, second ends of the bundle of optical fibers formed into a second shape having a second width greater than the first width, the tail end being constructed and arranged to focus a narrow elongated line of light on a workpiece; and
wherein the reflector defines a partial elliptical cylinder elongated in a direction of elongation over a second width that is greater than the first width, and defining a substantially constant partial elliptical cross-section taken transversely to the direction of elongation, the partial elliptical cross section defining a major axis, a minor axis an adjacent focus point on the major axis and a minor focus point on the major axis and the light element is located on the major axis with the two base wires extending from a base on the reflector so that the filament extends between the two base wires approximately parallel to the direction of elongation at the adjacent focus point and at an appproximate midpoint along the second width, and the inlet is located about the major axis at the remote focus point so that the inlet overlaps the reflector, the reflector and the light element being constructed and arranged to generate the narrow elongated line of light having a characteristic angular distribution in which a greater intensity of light is oriented at an angle adjacent the predetermined wide angle and a lesser intensity of light is oriented at an angle adjacent the line perpendicular to the optical plane of the wide-angle lens.

14. The illumination assembly as set forth in claim 13 wherein the inlet defines optical plane and the optical plane is oriented perpendicularly to the major axis.

15. The illumination assembly as set forth in claim 14 wherein the partial elliptical cylinder includes a pair of end caps each having a reflective surface, each being located at and covering an opposite end of the partial elliptical cylinder and being substantially flat.

16. In a machine vision system having a camera with a wide-angle lens for viewing a predetermined width of a workpiece based upon a predetermined field, of view, an illumination assembly that improves resolution of a viewed image by the camera at remote, opposing edges of the field of view, the opposing edges being oriented at a predetermined wide-angle to a line perpendicular to an optical plane of the lens, the illumination assembly comprising:
an illumination source that includes a concave reflector having a light element located within an enclosed portion of the reflector;
a fiber optic cable having a head end defining an inlet, the head end located to receive reflected light from the reflector and a tail end located to focus a narrow elongated line of light on a workpiece;
wherein the reflector defines a partial elliptical cylinder elongated in a direction of elongation and defining a substantially constant partial elliptical cross-section taken transversely to the direction of elongation the partial elliptical cross section defining a major axis, a minor axis an adjacent focus point on the major axis and a minor focus point on the major axis;

wherein the light element is located on the major axis, centered along the direction of elongation at the adjacent focus point and the inlet is centered about the major axis at the remote focus point and the inlet defines an optical plane and the optical plane is oriented perpendicularly to the major axis, the reflector and the light element being constructed and arranged to generate the narrow elongated line of light having a characteristic angular distribution in which a greater intensity of light is oriented at an angle adjacent the predetermined wide angle and a lesser intensity of light is oriented at an angle adjacent the line perpendicular to the optical plane of the lens; and a pair of end caps each having a reflective surface, each being located at and covering an opposite end of the partial elliptical cylinder and being substantially flat, wherein the end caps are located adjacent each of opposite edges of the inlet whereby light transmission into the inlet is maximized.

17. The illumination assembly as set forth in claim 13 wherein the line of light includes edges and a center region relative to the edges and wherein the camera is positioned so that an optical axis perpendicular to an optical plane of the camera passes through the line at a location along the line remote from the center region.

* * * * *